(12) United States Patent
Fish et al.

(10) Patent No.: US 10,023,511 B2
(45) Date of Patent: Jul. 17, 2018

(54) PROCESS FOR THE PRODUCTION OF ETHYLENE, VINYLIDENE, AND HYDROGEN CHLORIDE FROM ETHANE

(71) Applicant: Dow Global Technologies LLC, Midland, MI (US)

(72) Inventors: Barry B. Fish, Lake Jackson, TX (US); Matthew T. Pretz, Lake Jackson, TX (US); Max M. Tirtowidjojo, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/525,352

(22) PCT Filed: Nov. 10, 2015

(86) PCT No.: PCT/US2015/059886
§ 371 (c)(1),
(2) Date: May 9, 2017

(87) PCT Pub. No.: WO2016/077305
PCT Pub. Date: May 19, 2016

(65) Prior Publication Data
US 2017/0334812 A1 Nov. 23, 2017

Related U.S. Application Data

(60) Provisional application No. 62/078,024, filed on Nov. 11, 2014.

(51) Int. Cl.
*C07C 17/10* (2006.01)
*C07C 5/44* (2006.01)
*C07C 21/08* (2006.01)
*C01B 7/01* (2006.01)

(52) U.S. Cl.
CPC ............... *C07C 17/10* (2013.01); *C01B 7/01* (2013.01); *C07C 5/44* (2013.01); *C07C 21/08* (2013.01)

(58) Field of Classification Search
CPC ......... C07C 17/00; C07C 17/10; C07C 21/06; C07C 21/08
See application file for complete search history.

(56) References Cited

U.S. PATENT DOCUMENTS

| | | | |
|---|---|---|---|
| 2,628,259 | A | 2/1953 | Dirstine et al. |
| 2,979,541 | A | 4/1961 | Pitt et al. |
| 3,166,601 | A | 1/1965 | Taylor |
| 3,278,629 | A | 10/1966 | Hartnett |
| 3,304,337 | A | 2/1967 | Jordan, Jr. et al. |
| 4,119,674 | A | 10/1978 | Boozalis et al. |
| 5,097,083 | A | 3/1992 | Stauffer |
| 2007/0112234 | A1 | 5/2007 | Kim et al. |

FOREIGN PATENT DOCUMENTS

| | | | |
|---|---|---|---|
| DE | 1092903 B | | 11/1960 |
| GB | 734131 | * | 11/1952 |
| GB | 1345553 A | | 1/1974 |
| WO | 19900008116 A1 | | 7/1990 |
| WO | 1995026811 A1 | | 10/1995 |

* cited by examiner

*Primary Examiner* — Jafar F Parsa
(74) *Attorney, Agent, or Firm* — Tifani M. Edwards

(57) ABSTRACT

A process is provided for the chlorination of ethane using chlorine as the chlorinating agent to produce vinylidene (1,1-dichloroethylene), hydrogen chloride and ethylene.

13 Claims, 1 Drawing Sheet

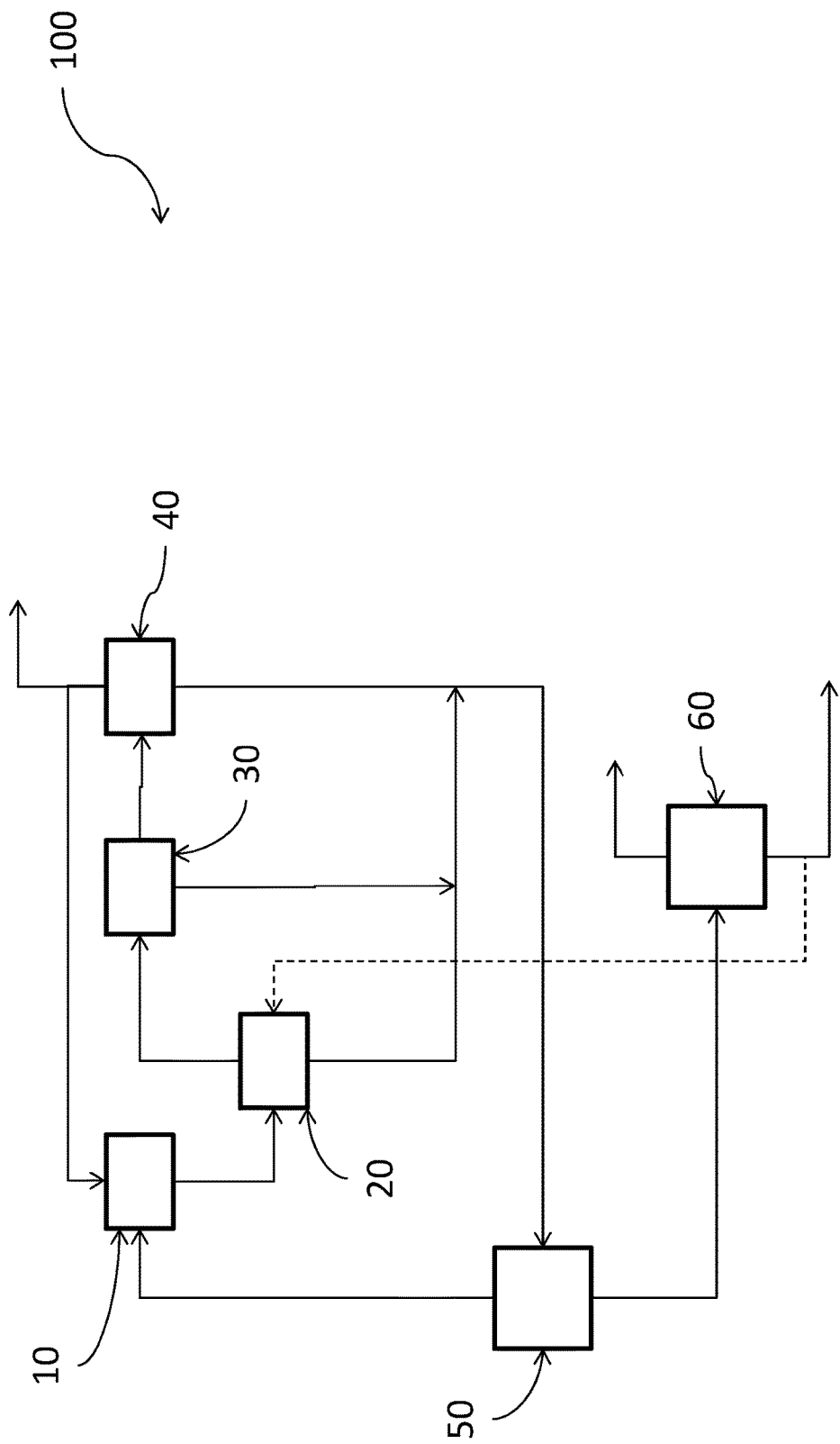

PROCESS FOR THE PRODUCTION OF ETHYLENE, VINYLIDENE, AND HYDROGEN CHLORIDE FROM ETHANE

The present invention relates to a method of producing vinylidene (1,1-dichloroethylene), hydrogen chloride, and ethylene by thermal chlorination of ethane using chlorine ($Cl_2$) as the chlorinating agent. The invention further relates to the recycling to extinction of ethyl chloride and vinyl chloride (VCM).

U.S. Pat. No. 3,278,629 discloses that it is well known that olefins can be obtained by thermal decomposition of petroleum-derived hydrocarbons. Ethylene can be obtained, for example, by thermal conversion of light saturated hydrocarbons such as ethane and/or propane. However, the prior art teaches that in such a process, the gaseous conversion product contains, in addition to the desired ethylene, significant amounts of other products such as methane, propylene, acetylene, butenes, and the like. In order to recover the ethylene in sufficiently pure form for its utilization, the gaseous thermal conversion product must be processed by fractionation in a series of steps requiring fairly elaborate equipment and time consuming operations. Furthermore, non-gaseous hydrocarbons such as oils and tars and normally cyclic hydrocarbons are formed simultaneously with the ethylene. Provision must-be made for removal of such contaminants because they lead to fouling of the apparatus and equipment. Thus, despite extensive studies which have been made on cracking of light hydrocarbons to produce ethylene, there are still some disadvantages in commercial production by this method.

U.S. Pat. No. 3,278,629 further discloses some of the problems inherent in the production of ethylene by cracking techniques can be obviated by producing this hydrocarbon in a relatively pure state by catalytic dehydrogenation of ethane.

However, the art has thus far failed to provide a continuous process for the dehydrogenation of ethane to ethylene which is not subject to a number of drawbacks. A process wherein conversion of ethane to ethylene can be effected with fewer operational steps and less byproduct formation is greatly needed.

It is therefore an object of the present invention to provide a method for the chlorination of ethane that overcomes the disadvantages of the conventional methods.

The present invention provides a continuous process for producing vinylidene, hydrogen chloride and ethylene comprising:
a) reacting a feed comprising chlorine with ethane in a reaction zone to produce a crude product wherein the crude product comprises
   i. a partial recycle fraction comprising ethylene and hydrogen chloride,
   ii. an extinction recycle fraction comprising ethyl chloride and vinyl chloride,
   iii. and product components vinylidene;
b) fractionally separating from the crude product the partial recycle fraction; and
c) fractionally separating the extinction recycle fraction from the remaining crude product.

As used herein "adiabatic" means: the chlorination process or reaction occurs without transfer of heat between the reactor and its surroundings. The process is said to be nearly adiabatic because the reactor is insulated or designed in such a manner that heat is not intentionally added or removed from the reactor.

As used herein "exit temperature" means: the temperature of reactor effluent. The chlorine to ethane feed ratio is one of the variables used to control the exit temperature. This chlorine:ethane molar ratio ranges from 1.1 to 2.0, alternatively from 1.1 to 1.9. The exit temperature ranges from 350-700° C., alternatively from 375-675° C., further alternatively from 400-650° C.

As used herein "partial recycle fraction" means: hydrogen chloride and ethylene. The components of the partial recycle fraction are products of the present invention.

As used herein "extinction recycle fraction" means: a composition comprising VCM and ethyl chloride (EC.).

As used herein "product components" means: vinylidene. As used herein vinylidene is synonymous with vinylidene chloride and 1,1-dichloroethylene. Vinylidene is a product of the present invention.

As used herein "heavies" are defined as EDC (1,2-dichloroethane), ADI (1,1-dichloroethane), 111 (1,1,1-trichloroethane), BTRI (1,1,2-trichloroethane), trans (trans-1,2-dichloroethylene), cis (cis-1,2-dichloroethylene). Heavies are a product of the present invention.

As used herein "inlet temperature" means: the mixed temperature of all the feed stream components as they enter the reactor. The inlet temperature ranges from 200° C. to 350° C., alternatively from 250-330° C., further alternatively from 260-320° C.

As used herein "recycle to extinction" means: when a byproduct or an intermediate product is recycled at the same mass rate as produced and thus at steady state the intermediate or byproduct species is not removed or produced from the process. According to the present invention, the extinction recycle fraction may optionally be recycled to extinction. Preferably the extinction recycle fraction is recycled to extinction.

All range values provided herein are inclusive and combinable. All percentages are percentages by weight.

FIG. 1 is a schematic view of the operation of a preferred embodiment of the process of the invention. Referring to the FIGURE, the process of the present invention is carried out as follows.

A feed containing components of ethane and chlorine is fed to a reactor ("reaction zone"). The feed may be substantially free of ethylene, alternatively free of ethylene. The feed components are preheated either individually or in combination in any manner and at any time prior to entry into the reactor 10. Prior art reference, CA 2097434 premixes ethane and chlorine below 200° C. and heats the mixture after adding it to the reactor. This method requires heat exchangers and thus is more capital intensive than the process of the present invention which uses a reactor 10 that is nearly adiabatic. Chlorine may be preheated to the inlet temperature or alternatively may comprise a temperature ranging from 20° to 80° C. before it is combined with the ethane and/or the partial recycle fraction. The chlorine may be co-fed into the reactor 10 with the ethane, mixed with the partial recycle fraction and then added to the reactor 10, or added by other conventional means of introducing materials into a reactor.

Conventional reactors may be used. One suitable example of a reactor is a jet-stirred reactor. The temperature of the reactor 10 at the time of entry of feed ("inlet temperature") ranges from 200-350° C., alternatively from 250-330° C., further alternatively from 260-320° C. The thermal chlorination reaction is carried out in the reactor 10. The chlorine is highly reactive with the ethane and reacts to produce a crude product comprising a partial recycle fraction, an extinction recycle fraction, product components, and heavies.

With the near adiabatic reactor condition, the exothermic reaction increases the crude product to temperatures higher than 350° C. up to 700° C. This vapor crude product is cooled to produce vapor phase and liquid reactor effluent. Suitable cooling methods include heat exchanging with coolant or adjusting feed ratios.

The vapor phase and liquid reactor effluent are cooled further in a condenser 20 to condense the liquid. The liquid is provided preferably to a distillation column 40, or alternatively to a separation column 50. The vapor phase is compressed in the compressor 30 at a pressure greater than or equal to 689 kPa, alternatively greater than or equal to 1378 kPa and further alternatively greater than or equal to 1930 kPa for efficient separation of partial recycle fraction comprising ethylene and HCl from the reactor crude effluents before being fed to the distillation column 40.

The use of a partial condenser on overheads of distillation column 40 is preferred in the separation of the partial recycle fraction from the crude products, since this provides a lower refrigeration load and hence lower operating cost as opposed to the use of total condenser. The partial recycle fraction is fractionally separated from the crude product and a portion of the partial recycle fraction can be returned to the reaction zone 10. The remaining of the partial recycle fraction product distillation column 40 overhead stream can be further fed to an Oxychlorination reactor where HCl and ethylene are catalytically converted to EDC (Oxy EDC reactor) to produce EDC. Additional HCl and ethylene can be accordingly fed to this OxyEDC reactor to match the required feed stoichiometry and thus lowering the raw material for the EDC production. Alternatively, additional HCl and/or ethylene can be fed to this OxyEDC reactor to increase the capacity in addition to the raw materials provided by the ethane chlorination process. Furthermore, the overheads of distillation column 40 can be wholly or partially fed to an additional separation column or an HCl absorber to separate ethylene from HCL to enable use of the components independently.

The crude product without the partial recycle fraction is the distillation column 40 bottom stream and is further fed to separation column 50 where extinction recycle fraction is separated from the product components and heavies. The overhead stream of separation column 50 comprising the extinction recycle fraction is optionally recycled into reactor 10 as it continuously, undergoes thermal chlorination with ethane chlorine to produce products comprising primarily vinylidene, hydrogen chloride and ethylene. Preferably the extinction recycle fraction is recycled to extinction by sending the entire stream to reaction zone 10. The reaction the present invention and specifically, the reaction of ethane, chlorine, and recycle streams is occurring in a continuous process.

The remaining crude product of the separation column 50 bottom stream (product components and heavies) is fed to column 60 where the vinylidene chloride is separated and purified from the heavies stream. The overheads of column 60 can be sold directly as vinylidene product or further purified as need. The bottom stream of column 60 is the partial recycle fraction that can be partially recycled to quench unit 20 to condense liquid product and/or partially recycled to reactor 10. The rest of the partial recycle fraction stream comprising heavies can be fed to a down-stream product to produce perchloroethylene.

The reaction of the present invention is highly efficient as greater than 95% and alternatively greater than 99% of the chlorine is converted during the reaction.

In addition the reaction of the present invention converts greater than 90% of the ethane and alternatively greater than 95% of the ethane is converted during the reaction.

EXAMPLE 1

Process for the Chlorination of Ethane

Ethane is chlorinated to produce ethylene, HCl, vinylidene, and VCM in a thermal chlorination jet-stirred reactor. The jet-stirred reactor was simulated as described in Chapter 8.7 in "Cleaner Combustion: Developing Detailed Kinetics Models," F. Battin-Leclerc, J. M. Simmie, E. Blurock (Ed) (2013)) using kinetics reported by Dahl et al. [Ind. Eng. Chem. Res. 2001, 40, 2226-2235]. The thermodynamic properties were obtained from reported literature values (see http://webbook.nist.gov/chemistry/) and thermochemical kinetics approach (see S. W. Benson "Thermochemical Kinetics: Methods for the Estimation of Thermochemical Data and Rate Parameters," 1976). The reactor model was imbedded inside a process flow sheet simulation (see http://www.aspentech.com/products/aspen-plus.aspx) such that impacts of recycle were evaluated.

The reactor has pressure of 40 psia and the feed is preheated to higher than 200° C. The reactor exit temperature is maintained by adjusting chlorine flow rate. The residence time is about 0.5 sec to 1 second depending on whether outlet or inlet flow rate is used, respectively. The crude product composition is given below in Table 1.

TABLE 1

Crude Liquid Product Results Without Partial Recycle Fraction to the Reactor

| | |
|---|---|
| $Cl_2$/ethane molar ratio | 1.49 |
| Partial Recycle Fraction Recycle/fresh ethane, mass ratio | 0 |
| Extinction recycle fraction recycle/fresh ethane, mass ratio | 5.53 |
| Reactor flow/reactor volume, kgmoles/hr/m^3 | 275 |
| Inlet Temperature | 269 |
| Outlet Temperature | 521 |
| Chlorine Conversion | >99 |
| Ethane Conversion | >99 |
| Total Product Composition, wt % | |

| | |
|---|---|
| HCl | 67.2 |
| Ethylene | 14.3 |
| Other | 1.6 |
| Vinylidene | 9.2 |
| Heavies | 7.7 |

| Heavies, wt % | Wt % |
|---|---|
| EDC | 0.3 |
| ADI | 5.3 |
| 111 | 55.8 |
| BTRI | 7.2 |
| trans | 15.1 |
| cis | 15.4 |

EXAMPLE 2

Fresh ethane and chlorine are fed to a reactor with a recycle to extinction fraction stream comprising ECl and vinyl chloride. The product is separated into a partial recycle fraction stream comprising ethylene, HCl, and unreacted ethane, and a crude product stream. In this case, about 40% of the partial recycle fraction is recycled back to the reactor, and the rest is taken out as product. The crude product is separated into the recycle to extinction (ECl/vinyl chloride) fraction which is recycled back to the reactor, and a crude product. ECl and vinyl chloride build to steady state level until no net production occurs in the reactor. Note that with the partial recycle fraction, the process results in less ethylene production and more production 1,1-dichloroethylene and heavies as compared to those in Example 1.

The operating conditions, recycle rates, and product composition are given in Table 2.

TABLE 2

Operating Conditions and Product Composition Results for Partial Recycle Fraction to the Reactor

| | |
|---|---|
| Cl$_2$/Ethane (molar ratio) | 2.06 |
| Partial Recycle Fraction/Fresh Ethane, (mass ratio) | 2.94 |
| Extinction Recycle Fraction/Fresh Ethane, (mass ratio) | 9.44 |
| Reactor Flow/Reactor Volume, kgmoles/hr/m$^3$ | 539 |
| Inlet Temperature | 278 |
| Outlet Temperature | 522 |
| Chlorine Conversion | >99 |
| Ethane Conversion | >99 |
| Total Product Composition, wt % | |
| HCl | 63.0 |
| Ethylene | 7.0 |
| Other | 1.1 |
| Vinylidene | 16.5 |
| Heavies | 12.4 |

| Heavies, wt % | Wt % |
|---|---|
| EDC | 0.4 |
| ADI | 1.0 |
| 111 | 51.4 |
| BTRI | 8.8 |
| trans | 18.1 |
| cis | 18.7 |

We claim:

1. A continuous process for producing vinylidene, hydrogen chloride and ethylene comprising:
   a) reacting a feed comprising chlorine with ethane in a reaction zone to produce a crude product wherein the crude product comprises
      i. a partial recycle fraction comprising ethylene and hydrogen chloride,
      ii. an extinction recycle fraction comprising ethyl chloride and vinyl chloride,
      iii. and product components vinylidene;
   b) fractionally separating from the crude product the partial recycle fraction; and
   c) fractionally separating the extinction recycle fraction from the remaining crude product wherein the molar ratio of chlorine to ethane in the feed is from 1.1 to 1.9 and further wherein the crude product comprises greater than 60% hydrogen chloride.

2. The process of claim 1 wherein the extinction recycle fraction is returned to the reaction zone.

3. The process of claim 1 wherein at least a portion of the partial recycle fraction is recycled to the reaction zone.

4. The process of claim 1 wherein the reaction is conducted at near adiabatic condition.

5. The process of claim 1 wherein the reactor comprises an inlet temperature ranges from 250-350° C.

6. The process of claim 1 wherein the reactor comprises an exit temperature ranging from 350-700° C.

7. The process of claim 1 wherein the feed stream components are pre-mixed prior to being fed in the reactor.

8. The process of claim 1 wherein the feed is not pre-mixed prior to being fed in the reactor and mixed as they entered the reactor.

9. The process of claim 1 further wherein greater than 95% of the chlorine is converted into products.

10. The process of claim 1 wherein greater than 95% of ethane is converted into products.

11. The process of claim 10 further wherein greater than 95% of ethane is converted into products.

12. The process of claim 1 wherein hydrogen chloride, vinylidene, heavies and ethylene are products.

13. The process of claim 1 wherein the heavies stream is partially recycled to quench reactor effluent.

* * * * *